(12) United States Patent
Hodges et al.

(10) Patent No.: US 6,179,979 B1
(45) Date of Patent: Jan. 30, 2001

(54) ELECTROCHEMICAL CELL

(75) Inventors: Alastair McIndoe Hodges, Blackburn South; Thomas William Beck, South Windsor; Oddvar Johansen, Mulgrave; Ian Andrew Maxwell, Leichhardt, all of (AU)

(73) Assignee: USF Filtration & Separations Group, Inc., Timonium, MD (US)

( * ) Notice: Under 35 U.S.C. 154(b), the term of this patent shall be extended for 0 days.

(21) Appl. No.: 09/068,828

(22) PCT Filed: Nov. 15, 1996

(86) PCT No.: PCT/AU96/00724

§ 371 Date: Mar. 15, 1999

§ 102(e) Date: Mar. 15, 1999

(87) PCT Pub. No.: WO97/18464

PCT Pub. Date: May 22, 1997

(30) Foreign Application Priority Data

Nov. 16, 1995 (AU) .................................................. PN 6619

(51) Int. Cl.[7] .................................................. G01N 27/26
(52) U.S. Cl. .......................... 204/403; 204/416; 427/2.11
(58) Field of Search .................................. 204/403, 416, 204/286, 290 R; 427/2.11

(56) References Cited

U.S. PATENT DOCUMENTS

| | | | |
|---|---|---|---|
| 4,224,125 | 9/1980 | Nakamura et al. | 204/195 B |
| 4,233,029 | 11/1980 | Columbus | 23/230 R |
| 4,254,083 | 3/1981 | Columbus | 422/55 |
| 4,259,165 | 3/1981 | Miyake | 204/415 |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,307,188 | 12/1981 | White | 435/4 |
| 4,374,013 | 2/1983 | Enfors | 204/195 |
| 4,404,066 | 9/1983 | Johnson | 204/1 |
| 4,431,004 | 2/1984 | Bessman et al. | 128/635 |
| 4,508,613 | * 4/1985 | Busta et al. | 204/418 |
| 4,517,287 | 5/1985 | Scheibe et al. | 435/4 |
| 4,517,291 | 5/1985 | Seago | 435/14 |
| 4,533,440 | 8/1985 | Kim | 204/1 |
| 4,545,382 | 10/1985 | Higgins et al. | 128/635 |

(List continued on next page.)

FOREIGN PATENT DOCUMENTS

| | | |
|---|---|---|
| 31042/93 | 7/1993 | (AU) . |
| 3103 464 A1 | 8/1982 | (DE) . |
| 3103-464 | 8/1982 | (DE) . |
| 0 251 915 A2 | 1/1988 | (EP) . |

OTHER PUBLICATIONS

Derwent Abstract Accession No. 92 119462/15, Class S03, JP,A, 04–62463 (Tokyo Yogyo K.K.) Feb. 27, 1992.

Patent Abstracts of Japan, P–269, p. 166, JP, A,59–3345 (Hitachi Seisakusho K.K.) Jan. 10, 1994.

*Primary Examiner*—T. Tung
*Assistant Examiner*—Alex Noguerola
(74) *Attorney, Agent, or Firm*—Knobbe, Martens, Olson and Bear LLP

(57) ABSTRACT

A method of manufacture of a thin layer electrochemical cell (FIGS. 12, 14) comprising the steps of: forming an aperture (11) extending through a sheet (1) of electrically resistive material, said aperture defining a side wall of the cell; mounting a first thin electrode layer (13) to one side of the sheet and extending over aperture (11) whereby to define a cell first end wall; mounting a second thin electrode layer (13) to the other side of the sheet and extending over aperture (11) whereby to define a second cell end wall in substantial overlying registration with the first electrode; and providing means (16) for admission of a liquid into the cell.

51 Claims, 3 Drawing Sheets

U.S. PATENT DOCUMENTS

| | | |
|---|---|---|
| 4,552,840 | 11/1985 | Riffer .................................. 205/778 |
| 4,629,563 | 12/1986 | Wrasidlo ........................ 210/500.34 |
| 4,654,197 | 3/1987 | Lilja et al. .............................. 422/56 |
| 4,664,119 | 5/1987 | Bessman et al. .................... 204/415 |
| 4,711,245 | 12/1987 | Higgins et al. ...................... 128/635 |
| 4,774,039 | 9/1988 | Wrasidlo ................................ 264/41 |
| 4,790,925 | 12/1988 | Miller et al. ......................... 204/415 |
| 4,900,424 | 2/1990 | Birth et al. ........................... 204/409 |
| 4,919,770 | 4/1990 | Preidel et al. ...................... 204/153.1 |
| 4,963,815 | 10/1990 | Hafeman ........................... 205/777.5 |
| 5,059,908 | 10/1991 | Mina .................................... 324/444 |
| 5,064,516 | 11/1991 | Rupich ................................ 204/415 |
| 5,120,420 | 6/1992 | Nankai et al. ....................... 204/403 |
| 5,122,244 | 6/1992 | Hoenes et al. .................... 204/153.1 |
| 5,126,034 | 6/1992 | Carter et al. ........................ 204/403 |
| 5,128,015 | 7/1992 | Szuminsky et al. ................. 204/403 |
| 5,141,868 | 8/1992 | Shanks et al. ....................... 435/288 |
| 5,151,166 | 9/1992 | Harral et al. ........................ 204/425 |
| 5,192,415 | 3/1993 | Yoshioka et al. .................... 204/403 |
| 5,229,282 | 7/1993 | Yoshioka et al. .................... 435/177 |
| 5,272,087 | 12/1993 | El Murr et al. ..................... 435/291 |
| 5,320,732 | 6/1994 | Nankai et al. ....................... 204/403 |
| 5,382,346 | 1/1995 | Uenoyama et al. ................. 204/403 |
| 5,384,028 | 1/1995 | Ito ....................................... 204/403 |
| 5,385,846 | 1/1995 | Kuhn et al. ............................ 436/70 |
| 5,413,690 | 5/1995 | Kost et al. ........................... 204/403 |
| 5,437,999 * | 8/1995 | Diebold et al. .................... 435/287.9 |
| 5,508,171 | 4/1996 | Walling et al. .................... 205/777.5 |
| 5,509,410 | 4/1996 | Hill et al. ............................. 128/637 |
| 5,527,446 | 6/1996 | Kosek et al. ......................... 204/415 |
| 5,567,302 | 10/1996 | Song et al. ........................ 205/777.5 |
| 5,611,908 | 3/1997 | Mattiessen et al. ................. 205/775 |
| 5,620,579 | 4/1997 | Genshaw et al. .................... 204/402 |
| 5,628,890 | 5/1997 | Carter et al. ........................ 204/403 |
| 5,645,709 | 7/1997 | Birch et al. .......................... 205/775 |

U.S. PATENT DOCUMENTS

| | | |
|---|---|---|
| 0 255 291 A1 | 2/1988 | (EP) . |
| 0 266 204 A2 | 4/1988 | (EP) . |
| 0 278 647 A2 | 8/1988 | (EP) . |
| 0 351 516 A2 | 1/1990 | (EP) . |
| 0 351 892 A2 | 1/1990 | (EP) . |
| 0 171 375 A1 | 5/1990 | (EP) . |
| 0 400 918 A1 | 12/1990 | (EP) . |
| 0 418 404 A1 | 3/1991 | (EP) . |
| 0 451 981 A2 | 10/1991 | (EP) . |
| 0 560 336 A1 | 9/1993 | (EP) . |
| 2 020 424 | 11/1979 | (GB) . |
| 2 154 735 | 9/1985 | (GB) . |
| 2 201 248 | 8/1988 | (GB) . |
| 3-167464 | 7/1991 | (JP) . |
| 4-66112 | 3/1992 | (JP) . |
| 1351-627 | 11/1987 | (SU) . |
| WO 89/08713 | 9/1989 | (WO) . |
| WO 92/15701 | 9/1992 | (WO) . |
| WO 94/02842 | 2/1994 | (WO) . |
| WO 95/16198 | 6/1995 | (WO) . |

* cited by examiner

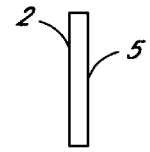
FIG. 1  FIG. 3
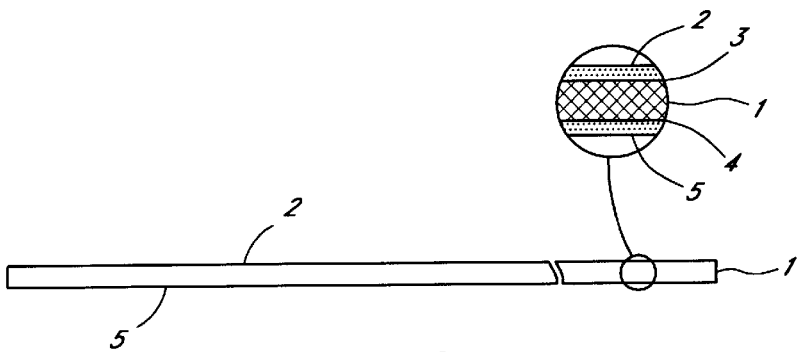
FIG. 2
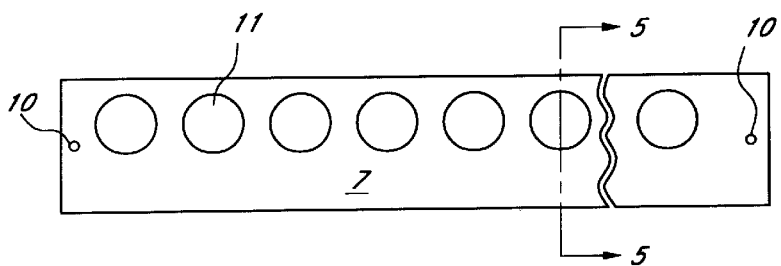
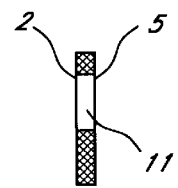
FIG. 4  FIG. 5

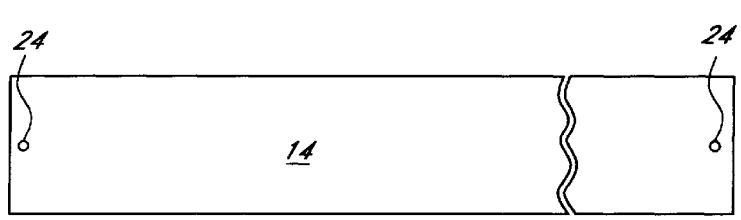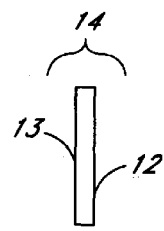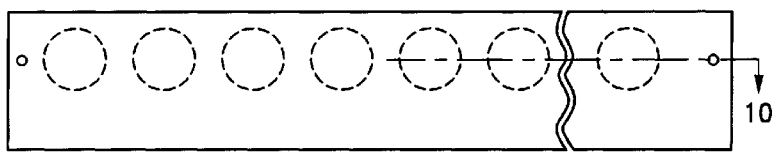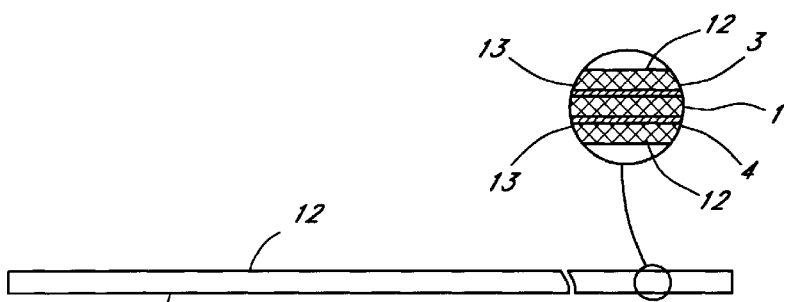

ELECTROCHEMICAL CELL

FIELD OF THE INVENTION

This invention relates to an electrochemical cell for determining the concentration of an analyte in a carrier.

BACKGROUND ART

The invention herein described is an improvement in or modification of the invention described in our co-pending application U.S. Ser. No. 08/981,385 filed Apr. 17, 1998, the contents of which are incorporated herein by reference.

The invention will herein be described with particular reference to a biosensor adapted to measure the concentration of glucose in blood, but it will be understood not to be limited to that particular use and is applicable to other analytic determinations.

It is known to measure the concentration of a component to be analysed in an aqueous liquid sample by placing the sample into a reaction zone in an electrochemical cell comprising two electrodes having an impedance which renders them suitable for amperometric measurement. The component to be analysed is allowed to react directly or indirectly with a redox reagent whereby to form an oxidisable (or reducible) substance in an amount corresponding to the concentration of the component to be analysed. The quantity of the oxidisable (or reducible) substance present is then estimated electrochemically. Generally this method requires sufficient separation of the electrodes so that electrolysis products at one electrode cannot reach the other electrode and interfere with the processes at the other electrode during the period of measurement.

In our co-pending application we described a novel method for determining the concentration of the reduced (or oxidised) form of a redox species in an electrochemical cell of the kind comprising a working electrode and a counter (or counter/reference) electrode spaced from the working electrode by a predetermined distance. The method involves applying an electric potential difference between the electrodes and selecting the potential of the working electrode such that the rate of electro-oxidation of the reduced form of the species (or of electro-reduction of the oxidised form) is diffusion controlled. The spacing between the working electrode and the counter electrode is selected so that reaction products from the counter electrode arrive at the working electrode. By determining the current as a function of time after application of the potential and prior to achievement of a steady state current and then estimating the magnitude of the steady state current, the method previously described allows the diffusion coefficient and/or the concentration of the reduced (or oxidised) form of the species to be estimated.

Our co-pending application exemplifies this method with reference to use of a "thin layer electrochemical cell" employing a GOD/Ferrocyanide system. As herein used, the term "thin layer electrochemical cell" refers to a cell having closely spaced electrodes such that reaction product from the counter electrode arrives at the working electrode. In practice, the separation of electrodes in such a cell for measuring glucose in blood will be less than 500 microns, and preferably less than 200 microns.

The chemistry used in the exemplified electrochemical cell is as follows:

where GOD is the enzyme glucose oxidase, and GOD* is the 'activated' enzyme. Ferricyanide ($[Fe(CN)_6]^{3-}$) is the 'mediator' which returns the GOD* to its catalytic state. GOD, an enzyme catalyst, is not consumed during the reaction so long as excess mediator is present. Ferrocyanide ($[Fe(CN)_6]^{4-}$) is the product of the total reaction. Ideally there is initially no ferrocyanide, although in practice there is often a small quantity. After reaction is complete the concentration of ferrocyanide (measured electrochemically) indicates the initial concentration of glucose. The total reaction is the sum of reactions 1 and 2:

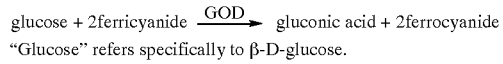

"Glucose" refers specifically to β-D-glucose.

The prior art suffers from a number of disadvantages. Firstly, sample size required is greater than desirable. It would be generally preferably to be able to make measurements on samples of reduced volume since this in turn enables use of less invasive methods to obtain samples.

Secondly, it would be generally desirable to improve the accuracy of measurement and to eliminate or reduce variations due, for example, to cell asymmetry or other factors introduced during mass production of microcells. Likewise, it would be desirable to reduce electrode "edge" effects.

Thirdly, since the cells are disposable after use, it is desirable that they be capable of mass production at relatively low cost.

SUMMARY OF THE INVENTION

According to one aspect the invention consists in a method of manufacture of an electrochemical cell comprising the steps of:

forming an aperture extending through a sheet of electrically resistive material, said aperture defining a side wall of the cell;

mounting a first thin electrode layer to one side of the sheet and extending over the aperture whereby to define a cell first end wall;

mounting a second thin electrode layer to the other side of the sheet and extending over the aperture whereby to define a cell second end wall in substantial overlying registration with the first electrode; and providing means for admission of a liquid into the cell defined between the side wall and said end walls.

The first and second electrode layers may be conductors or semi-conductors and may be the same or different. Noble metal electrode layers are preferred.

In preferred embodiments of the invention the aperture is of circular cross-section whereby the side wall is cylindrical and the first and second electrodes cover the aperture.

BRIEF DESCRIPTION OF THE DRAWINGS

The invention will now be particularly described by way of example only with reference to the accompanying schematic drawings wherein:

FIG. 1 shows the product of manufacturing step 2 in plan.

FIG. 2 shows the product of FIG. 1 in side elevation.

FIG. 3 shows the product of FIG. 1 in end elevation.

FIG. 4 shows the product of manufacturing step 3 in plan.

FIG. 5 shows the product of FIG. 4 in cross-section on line 5—5 of FIG. 4.

FIG. 6 shows the product of manufacturing step 5 in plan.

FIG. 7 shows the product of FIG. 6 in side elevation.

FIG. 8 shows the product of FIG. 6 in end elevation.

FIG. 9 shows the product of manufacturing step 7 in plan.

FIG. 10 is a cross-section of FIG. 9 on line 10—10.

FIG. 11 shows the product of FIG. 9 in end elevation.

DETAILED DESCRIPTION OF THE PREFERRED EMBODIMENTS

Figure 13:
FIG. 13 shows the cell of FIG. 12 in side elevation.

The construction of a thin layer electrochemical cell will now be described by way of example of the improved method of manufacture.

Step 1: A sheet of Melinex® (a chemically inert, and electrically resistive Polyethylene Terephthalate ["PET"]) approximately 13 cm×30 cm and 100 micron thick was laid flat on a sheet of release paper 2 and coated using a Number 2 MYAR bar to a thickness of 12 microns wet (approximately 2–5 microns dry) with a water-based heat activated adhesive 3 (ICI Novacoat system using catalyst:adhesive). The water was then evaporated by means of a hot air dryer leaving a contact adhesive surface. The sheet was then turned over on a release paper and the reverse side was similarly coated with the same adhesive 4, dried, and a protective release paper 5 applied to the exposed adhesive surface. The edges were trimmed to obtain a sheet uniformly coated on both sides with tacky contact adhesive protected by release paper.

Step 2: The sheet with protective release papers was cut into strips 7, each about 18 mm×210 mm (FIGS. 1–3).

Step 3: A strip 7 of adhesive-coated PET from step 2 with release paper 2, 5 on respective sides, was placed in a die assembly (not shown) and clamped. The die assembly was adapted to punch the strip with a locating hole 10 at each end and with for example 37 circular holes 11 each of 3.4 mm diameter at 5 mm centres equi-spaced along a line between locating holes 10. The area of each hole 11 is approximately 9 square mm.

Step 4: A sheet 12 of Mylar® PET approximately 21 cm square and 135 microns thick was placed in a sputter coating chamber for palladium coating 13. The sputter coating took place under a vacuum of between 4 and 6 millibars and in an atmosphere of argon gas. Palladium was coated on the PET to a thickness of 100–1000 angstroms. There is thus formed a sheet 14 having a palladium sputter coating 13.

Step 5: The palladium coated PET sheet 14 from Step 4 was then cut into strips 14 and 15 and a die was used to punch two locating holes 24 with the locating holes 10 of in each strip, at one end (FIGS. 6, 7 and 8). Strips 14 and 15 differ only in dimension strips 14 being 25 mm×210 mm and strips 15 being 23 mm×210 mm.

Step 6: A spacer strip 7 prepared as in step 3 was then placed in a jig (not shown) having two locating pin (one corresponding to each locating hole 10 of strip 7) and the upper release paper 2 was removed. A strip 14 of palladium coated PET prepared as in step 5 was then laid over the adhesive layer, palladium surface downwards, using the jig pins to align the locating holes 16 with the underlying PET strip 7. This combination was then passed through a laminator comprising a set of pinch rollers, one of which was adapted to heat the side bearing a palladium coated PET strip 14. The roller on the opposite side of the strip 7 was cooled. By this means, only the adhesive between the palladium of strip 14 and PET strip 7 was activated.

Step 7: PET strip 7 was then turned over and located in the jig with the release coating uppermost. The release coating was peeled off and second palladium coated strip 15 was placed palladium side down on the exposed adhesive surface using the locating pins to align the strips. this assembly was now passed again through the laminator of step 6, this time with the hot roll adjacent the palladium coated Mylar® added in step 7 so as to activate the intervening adhesive (FIGS. 9, 10 and 11).

Step 8: The assembly from step 7 was returned to the die assembly and notches 16 punched in locations so as to extend between the circular holes 11 previously punched in the Melinex® PET and the strip edge 17. Notches 16 extend so as to intercept the circumference of each circular cell. The strip was then guillotined to give 37 individual "sensor strips". each strip being about 5 mm wide and each having one thin layer cavity cell (FIGS. 12, 13 and 14).

Figure 12:
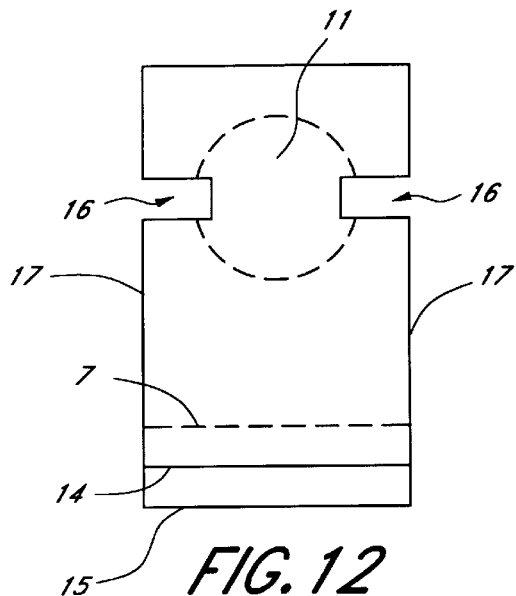
FIG. 12 shows a cell according to the invention in plan.
Figure 14:
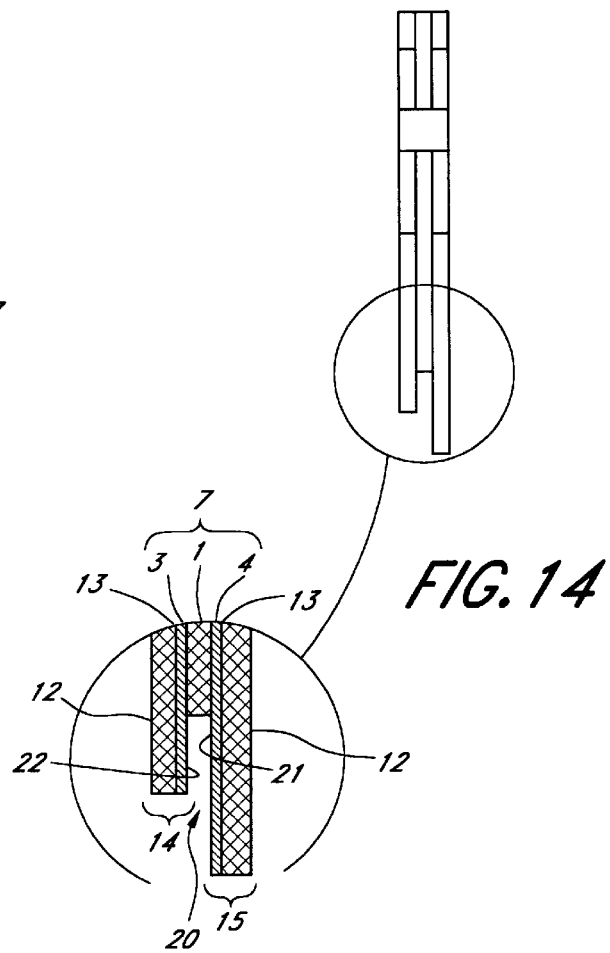
FIG. 14 shows the cell of FIG. 12 in end elevation.

There is thus produced a cell as shown in FIGS. 12, 13 or 14. The cell comprises a first electrode consisting of PET layer 12, a palladium layer 13, an adhesive layer 3, a PET sheet 1, a second adhesive layer 4, a second electrode comprising palladium layer 13, and a PET layer 12. Sheet 1 defines a cylindrical cell 11 having a thickness in the cell axial direction corresponding to the thickness of the Melinex® PET sheet layer 1 together with the thickness of adhesive layers 3 and 4. The cell has circular palladium end walls. Access to the cell is provided at the side edge of the cell where notches 16 intersect cell 11.

In preferred embodiments of the invention, a sample to be analysed is introduced to the cell by capillary action. The sample is placed on contact with notch 16 and is spontaneously drawn by capillary action into the cell, displaced air from the cell venting from the opposite notch 16. A surfactant may be included in the capillary space to assist in drawing in the sample.

The sensors are provided with connection means for example edge connectors whereby the sensors may be placed into a measuring circuit. In a preferred embodiment this is achieved by making spacer 1 shorter than palladium supporting sheets 14, 15 and by making one sheet 15 of shorter length than the other 14. This forms a socket region 20 having contact areas 21, 22 electrically connected with the working and counter electrodes respectively. A simple tongue plug having corresponding engaging conduct surfaces can then be used for electrical connection. Connectors of other form may be devised.

Chemicals for use in the cell may be supported on the cell electrodes or walls, may be supported on an independent support contained within the cell or may be self-supporting.

In one embodiment, chemicals for use in the cell are printed onto the palladium surface of the electrode immediately after step 1 at which stage the freshly-deposited palladium is more hydrophilic. For example, a solution containing 0.2 mylar potassium ferricyanide and 1% by weight of glucose oxidase dehydrogenase may be printed on to the palladium surface. Desirably, the chemicals are printed only in the areas which will form a wall of the cell and for preference the chemicals are printed on the surface by means of an ink jet printer. In this manner, the deposition of chemicals may be precisely controlled. If desired, chemicals which are desirably separated until required for use may be printed respectively on the first and second electrodes. For example, a GOD/ferrocyanide composition can be printed on one electrode and a buffer on the other. Although it is highly preferred to apply the chemicals to the electrodes prior to assembly into a cell, chemicals may also be introduced into the cell as a solution after step 6 or step 8 by pipette in the traditional manner and the solvent subsequently is removed by evaporation or drying. Chemicals need not be printed on the cell wall or the electrodes and may instead be impregnated into a gauze, membrane, non-woven fabric or the like contained within, or filling, the cavity (eg inserted in cell 11 prior to steps 6 or 7). In another embodiment the chemicals are formed into a porous mass which may be introduced into the cell as a pellet or granules. Alternatively, the chemicals may be introduced as a gel.

In a second embodiment of the invention a laminate 21 is first made from a strip 14 as obtained in step 5 adhesively sandwiched between two strips 7 as obtained from step 3. Laminate 20 is substituted for sheet 1 in step 5 and assembled with electrodes as in steps 6 and 7.

Figure 15:
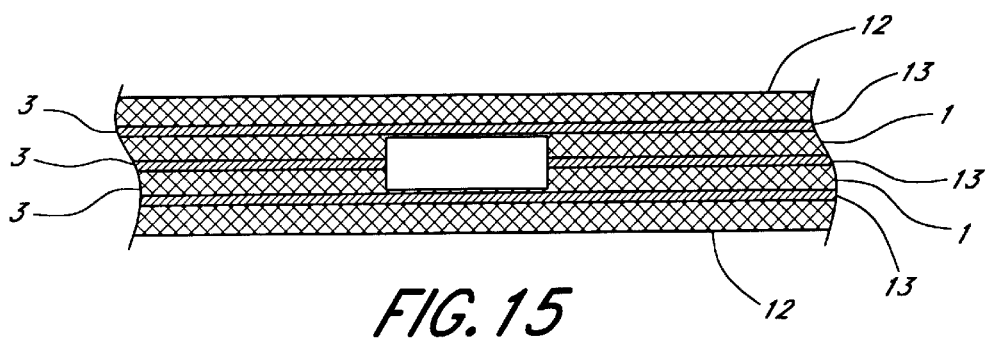
FIG. 15 shows a scrap portion of a second embodiment of the invention in enlarged section.

There is thus obtained a cell as shown in FIG. 15 which differs from that of FIGS. 9 to 11 in that the cell has an annular electrode disposed between the first and second electrode. This electrode can for example be used as a reference electrode.

It will be understood that in mass production of the cell, the parts may be assembled as a laminate on a continuous line. For example, a continuous sheet 1 of PET could be first punched and then adhesive could be applied continuously by printing on the remaining sheet. Electrodes (pre-printed with chemical solution and dried) could be fed directly as a laminate onto the adhesive coated side. Adhesive could then be applied to the other side of the punched core sheet and then the electrode could be fed as a laminate onto the second side.

The adhesive could be applied as a hot melt interleaving film. Alternatively, the core sheet could first be adhesive coated and then punched.

By drying chemicals on each electrode prior to the gluing step the electrode surface is protected from contamination.

Although the cell has been described with reference to Mylar® and Melinex® PET, other chemically inert and electrically resistive materials may be utilised and other dimensions chosen. The materials used for space sheet 1 and for supporting the reference and counter electrodes may be the same or may differ one from the other. Although the invention has been described with reference to palladium electrodes, other metals such as platinum, silver, gold, copper or the like may be used and silver may be reacted with a chloride to form a silver/silver chloride electrode or with other halides. The electrodes need not be of the same metal.

Although the use of heat activated adhesives has been described, the parts may be assembled by use of hot melt adhesives, fusible laminates and other methods.

The dimensions of the sensor may readily be varied according to requirements.

While it is greatly preferred that the electrodes cover the cell end openings, in other embodiments (not illustrated) the electrodes do not entirely cover the cell end openings. In that case it is desirable that the electrodes be in substantial overlying registration.

Preferred forms of the invention in which the electrodes cover the apertures of cell 11 have the advantages that the electrode area is precisely defined simply by punching hole 11. Furthermore the electrodes so provided are parallel, overlying, of substantially the same area, and are substantially or entirely devoid of "edge" effects.

Although in the embodiments described each sensor has one cell cavity, sensors may be provided with two or more cavities. For example, a second cavity may be provided with a predetermined quantity of the analyte and may function as a reference cell.

As will be apparent to those skilled in the art from the teaching herein contained, a feature of one embodiment herein described may be combined with features of other embodiments herein described or with other embodiments described in our co-pending application. Although the sensor has been described with reference to palladium electrodes and a GOD/ferrocyanide chemistry, it will be apparent to those skilled in the art that other chemistries, and other materials of construction may be employed without departing from the principles herein taught.

What is claimed is:

1. A method of manufacture of a thin layer electrochemical cell (as herein defined) comprising the steps of:
    forming an aperture extending through a sheet of electrically resistive material, said aperture defining a side wall of the cell and said aperture defining a working electrode area in the cell,
    mounting a first thin electrode layer to one side of the sheet and extending over the aperture whereby to define a cell first end wall,
    mounting a second thin electrode layer to the other side of the sheet and extending over the aperture whereby to define a second cell end wall in substantial overlying registration with the first electrode, and
    providing means for admission of a liquid into the cell defined between the side wall and said end walls.

2. A method according to claim 1 wherein at least one of the electrode layers is a nobel metal.

3. A method according to claim 2 wherein at least one of the electrode layers is palladium.

4. A method according to claim 1 wherein each of the metal electrode layers substantially covers the aperture.

5. A method according to claim 1 wherein the aperture is of circular cross-section, whereby the side-wall is cylindrical.

6. A method according to claim 1 wherein the means for admission of a liquid comprise a slot or passage communicating between the cell interior and an edge of the sheet.

7. A method according to claim 6, wherein the slot or passage is formed through the side wall and through the sheet of electrically resistive material.

8. A method according to claim 1 wherein at least one of the thin electrode layers is a sputter coated metal deposit.

9. A method according to claim 1 wherein the electrode layers are adhered to the sheet.

10. A method according to claim 1 wherein one or more chemicals for use in the cell are printed onto one or both electrode layers.

11. A method according to claim 1 wherein one or more chemicals for use in the cell are added in a solvent to the cell after one electrode layer has been mounted to the sheet and before the other electrode layer has been mounted to the sheet and wherein the solvent is subsequently evaporated to leave the chemicals in dry form in the cell.

12. A method according to claim 1 wherein one or more chemicals for use in the cell are contained in or on a support which is included within the cell.

13. A method according to claim 1 wherein one or more chemicals for use in the cell are contained within the cell in self-supporting form.

14. A method according to claim 1 wherein one or both electrode layers comprise a sputter coated metal and one or more chemicals for use in the cell are printed onto the metal surface immediately after the metal is sputter coated.

15. A method according to claim 14 wherein one or more chemicals for use in the cell are printed onto the metal surface by means of an ink jet printer.

16. A method according to claim 1, wherein one or more of the electrode layers and the sheet is provided with a formation adapted to interlock with a formation of another one of the electrode layers and the sheet or of an assembly jig.

17. A method according to claim 1, wherein the sheet of electrically resistive material comprises a laminate having two layers, each of electrically resistive and chemically resistant material, having a metal layer therebetween which in the final product is useful as a reference electrode disposed intermediate the first metal and the second metal.

18. A method according to claim 1, further comprising the step of providing means for venting of gas during the admission of liquid into the cell.

19. A method according to claim 1 wherein the second thin electrode layer is mounted in opposing relationship a distance of less than 200 microns from the first thin electrode layer.

20. A method of manufacture of an electrochemical cell comprising the steps of:
  depositing a first sputter coating of a metal on a first suitable substrate;
  depositing a second sputter coating of the same or a different metal on a second suitable substrate;
  forming an aperture in a sheet of electrically resistive material, said aperture defining a side wall of the cell and having openings on each face of the sheet and said aperture defining a working electrode area in the cell;
  adhering the first substrate to the sheet with the metal coating thereof adjacent one side of the sheet whereby to expose a portion of the first coating to one aperture opening and to provide a first electrode;
  adhering the second substrate to the sheet with the metal coating thereof adjacent the other side of the sheet whereby to expose a portion of the second coating to the other aperture opening facing the first and to provide a second electrode; and
  providing means for admission of a liquid into the cell defined between the side wall and said exposed portions of metal coating.

21. A method according to claim 20 wherein the means for admission of a liquid comprise a passage communicating between the cell interior and an edge of the sheet.

22. A method according to claim 20 wherein the first sputter coating and the second sputter coating are adhered to the sheet by means of an adhesive.

23. A method according to claim 22 wherein the adhesive is a heat activated adhesive.

24. A cell according to claim 20 wherein at least one reagent is provided on a sputter coated metal electrode.

25. A method according to claim 20 wherein the adhesive is a water-based adhesive.

26. A method according to claim 20 wherein the adhesive is a contact adhesive.

27. A method according to claim 20 wherein the adhesive is applied in a thickness of from 2 to 5 microns.

28. A method according to claim 20 wherein the adhesive is applied by means of a MYAR bar.

29. A method of manufacture of an electrochemical cell comprising the steps of:
  forming a plurality of first sputter coatings of metal on a first substrate;
  forming a plurality of second sputter coatings of metal on a second substrate;
  forming a plurality of apertures in a sheet of electrically resistive material, each aperture defining a side wall of a cell and each aperture defining a working electrode area in the cell;
  adhering the first substrate to the sheet with the metal coatings thereof adjacent one side of the sheet and defining first end walls of respective cells defined by the sheet;
  adhering the second substrate to the sheet with the metal coatings thereof adjacent the other side of the sheet and defining second cell end walls of respective cells defined in the sheet; and
  dividing the assembly into a plurality of cells.

30. An electrochemical cell comprising an electrically resistive substrate having a first thin layer of first metal on one face, a second electrically resistive substrate having a second thin layer of metal sputter coated on one face, said substrates being disposed with the metal coating of one facing the metal coating of the other and being separated by a sheet pierced by an aperture, the wall of which aperture cooperates with said metal coatings to define a cell wall, and wherein said aperture defines a working electrode area in the cell, and a sample introduction aperture whereby a solution may be introduced into the cell.

31. A cell according to claim 30, wherein the substrate is a Polyethylene Terephthalate.

32. A cell according to claim 30, wherein the sheet is of Polyethylene Terephthalate.

33. A cell according to claim 30 wherein at least one of the electrode layers comprises palladium.

34. A cell according to claim 30, wherein one of the sputtered metal layers is of silver.

35. A cell according to claim 30 wherein one of the layers is a metal coating of silver and is halogenised to produce a silver halide surface.

36. A cell according to claim 30 further comprising a second electrochemical cell, wherein said second electrochemical cell comprises a second aperture piercing the sheet, and wherein the second aperture is covered on at least one side of the sheet by the same metal layer as covers the first aperture on that side.

37. A cell according to claim 30 further comprising a second electrochemical cell, wherein said second electrochemical cell comprises a second aperture wherein the second aperture is covered on at least one side by a metal layer which is electrically insulated from the metal layer covering the first aperture on that side.

38. A thin layer electrochemical cell comprising
  an electrically resistive sheet pierced by an aperture wherein said aperture defines a working electrode area in the cell,
  a first electrode layer covering the aperture on one side of the sheet, a second electrode layer covering the aperture on the other side of the sheet, and a passage for admission into the aperture of a liquid.

39. A cell according to claim 38 wherein at least one electrode layer comprises a conductor.

40. A cell according to claim 30 wherein at least one electrode layer comprises a semi-conductor.

41. A cell according to claim 38 wherein at least one electrode layer comprises a noble metal.

42. A cell according to claim 38 wherein at least one electrode coating is palladium.

43. A cell according to claim 38 wherein an electrode comprises a sputter coated metal.

44. A cell according to claim 38 wherein the cell contains one or more reagents.

45. A cell according to claim 38 wherein one or more reagents are supported or impregnated in a carrier within the cell.

46. A cell according to claim 38 wherein one or more chemicals for use in the cell are contained within the cell in self-supporting form.

47. A cell according to claim 38 wherein at least one of the electrodes is a sputter coated palladium.

48. A cell according to claim 38 wherein the electrodes are of substantially the same area.

49. A cell according to claim 38 wherein the electrodes are in substantial registration one with the other.

50. A cell according to claim 38 further comprising means for venting of gas during admission of liquid into the cell.

51. A cell according to claim 38 wherein the second electrode layer is mounted in opposing relationship a distance of less than 200 microns from the first electrode layer.

* * * * *